(12) United States Patent
Johnson et al.

(10) Patent No.: US 7,501,399 B2
(45) Date of Patent: *Mar. 10, 2009

(54) IMMUNOEFFECTOR COMPOUNDS

(75) Inventors: David A. Johnson, Hamilton, MT (US); Jory Baldridge, Victor, CA (US); C. Gregory Sowell, Mukilteo, WA (US)

(73) Assignee: Corixa Corporation, Seattle, WA (US)

( * ) Notice: Subject to any disclaimer, the term of this patent is extended or adjusted under 35 U.S.C. 154(b) by 325 days.

This patent is subject to a terminal disclaimer.

(21) Appl. No.: 11/519,275

(22) Filed: Sep. 11, 2006

(65) Prior Publication Data

US 2007/0004914 A1 Jan. 4, 2007

Related U.S. Application Data

(62) Division of application No. 10/496,620, filed as application No. PCT/US01/24284 on Aug. 3, 2001, now Pat. No. 7,129,219.

(60) Provisional application No. 60/223,056, filed on Aug. 4, 2000.

(51) Int. Cl.
*A01N 43/04* (2006.01)
*A61K 49/04* (2006.01)

(52) U.S. Cl. .............................. 514/27; 514/23; 514/24; 514/25; 424/1.73; 424/9.43

(58) Field of Classification Search ...................... None
See application file for complete search history.

(56) References Cited

U.S. PATENT DOCUMENTS 6,525,028 B1 * 2/2003 Johnson et al. ............... 514/27
6,911,434 B2 * 6/2005 Baldridge et al. ............. 514/27

FOREIGN PATENT DOCUMENTS

WO  WO 98/50399 A1  11/1998

OTHER PUBLICATIONS

Johnson, et al.; "Synthesis and Biological evaluation of a new class of vaccine adjuvants: Aminoalkyl glucosaminide 4-phosphates (AGPs)"; *Bioorganic & Medicinal Chemistry Letters*; 1999; pp. 2273-2278; vol. 9; Elsevier Science Ltd.

* cited by examiner

*Primary Examiner*—Traviss C McIntosh, III
(74) *Attorney, Agent, or Firm*—Townsend and Townsend and Crew LLP

(57) ABSTRACT

This invention provides compounds containing a 2-deoxy-2-amino-β-D-glucopyranose (glucosamine) glycosidically linked to an cyclic aminoalkyl (aglycon) group. The invention further provides methods for inducing an immune response using the compounds of the present invention in the presence or absence of an antigen. In addition, methods for treating disease with the compounds of the present invention with or without an antigen are also provided in this invention.

27 Claims, No Drawings

IMMUNOEFFECTOR COMPOUNDS

This application is a division of U.S. patent application Ser. No. 10/469,620, filed Feb. 18, 2004, now U.S. Pat. No. 7,129,219, which is a 371 of PCT/US01/24284, filed Aug. 3, 2001, which claims the benefit of U.S. Provisional Patent Application No. 60/223,056, filed Aug. 4, 2000.

FIELD OF THE INVENTION

This invention relates generally to immunoeffector compounds, their use in pharmaceutical compositions, and methods for their production and their use in prophylactic and/or therapeutic vaccination. More particularly, the present invention relates to an adjuvant system comprising 2-deoxy-2-amino-β-D-glucopyranose (glucosamine)glycosidically linked to a cyclic aminoalkyl (aglycon) group.

BACKGROUND OF THE INVENTION

Humoral immunity and cell-mediated immunity are the two major branches of the mammalian immune response. Humoral immunity involves the generation of antibodies to foreign antigens. Antibodies are produced by B-lymphocytes. Cell-mediated immunity involves the activation of T-lymphocytes which either act upon infected cells bearing foreign antigens or stimulate other cells to act upon infected cells. Both branches of the mammalian immune system are important in fighting disease. Humoral immunity is the major line of defense against bacterial pathogens. In the case of viral disease, the induction of cytotoxic T lymphocytes (CTLs) appears to be crucial for protective immunity. Thus, an effective vaccine preferably stimulates both branches of the immune system to protect against disease.

Vaccines present foreign antigens from disease causing agents to a host so that the host can mount a protective immune response. Often, vaccine antigens are killed or attenuated forms of the microbes which cause the disease. The presence of non-essential components and antigens in these killed or attenuated vaccines has encouraged considerable efforts to refine vaccine components including developing well-defined synthetic antigens using chemical and recombinant techniques. The refinement and simplification of microbial vaccines, however, has led to a concomitant loss in potency. Low-molecular weight synthetic antigens, though devoid of potentially harmful contaminants, are often not sufficiently immunogenic by themselves. These observations have led investigators to add immune system stimulators known as adjuvants to vaccine compositions to potentiate the activity of the vaccine components.

Immune adjuvants are compounds which, when administered to an individual or tested in vitro, increase the immune response to an antigen in a subject to which the antigen is administered, or enhance certain activities of cells from the immune system. A number of compounds exhibiting varying degrees of adjuvant activity have been prepared and tested (see, for example, Shimizu et al. 1985, Bulusu et al. 1992, Ikeda et al. 1993, Shimizu et al. 1994, Shimizu et al. 1995, Miyajima et al. 1996). However, these and other prior adjuvant systems often display toxic properties, are unstable and/or have unacceptably low immunostimulatory effects.

Presently, the only adjuvant licensed for human use in the United States is alum, a group of aluminum salts (e.g., aluminum hydroxide, aluminum phosphate) in which vaccine antigens are formulated. Particulate carriers like alum reportedly promote the uptake, processing and presentation of soluble antigens by macrophages. Alum, however, is not without side-effects and is unfortunately limited to humoral (antibody) immunity only.

The discovery and development of effective adjuvant systems is essential for improving the efficacy and safety of existing and future vaccines. Thus, there is a continual need for new and improved adjuvant systems, particularly those that drive both effector arms of the immune system, to better facilitate the development of a next generation of synthetic vaccines. The present invention fulfills these and other needs.

SUMMARY OF THE INVENTION

The compounds of the present invention are immunoeffector molecules which enhance humoral and cell-mediated immune responses to vaccine antigens. The compounds comprise a 2-deoxy-2-amino-β-D-glucopyranose (glucosamine) glycosidically linked to an cyclic aminoalkyl (aglycon) group. The compounds are phosphorylated at the 4 or 6-position of the glucosamine ring and acylated with alkanoyloxytetradecanoyl residues on the aglycon nitrogen and the 2 and 3-positions of the glucosamine ring. The compounds of the subject invention are described generally by formula (I):

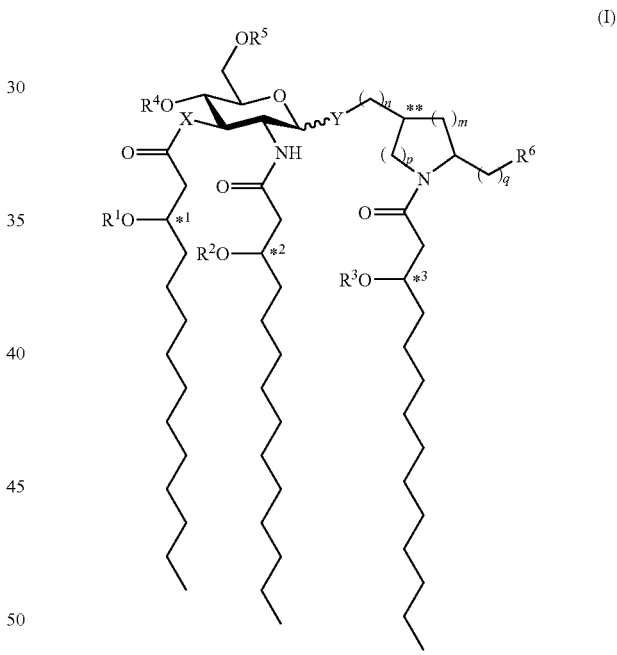

and pharmaceutically acceptable salts thereof, wherein X is —O— or —NH— and Y is —O— or —S—; $R^1$, $R^2$, and $R^3$ are each independently a ($C_2$-$C_{24}$)acyl group, including saturated, unsaturated and branched acyl groups; $R^4$ is —H or —$PO_3R^7R^8$, wherein $R^7$ and $R^8$ are each independently H or ($C_1$-$C_4$)alkyl; $R^5$ is —H, —$CH_3$ or —$PO_3R^9R^{10}$, wherein $R^9$ and $R^{10}$ are each independently selected from —H and ($C_1$-$C_4$)alkyl; $R^6$ is independently selected from H, OH, ($C_1$-$C_4$) alkoxy, —$PO_3R^{11}R^{12}$, —$OPO_3R^{11}R^{12}$, —$SO_3R^{11}$, —$OSO_3R^{11}$, —$NR^{11}R^{12}$, —$SR^{11}$, —CN, —$NO_2$, —CHO, —$CO_2R^{11}$, and —$CONR^{11}R^{12}$, wherein $R^{11}$ and $R^{12}$ are each independently selected from H and ($C_1$-$C_4$)alkyl; with the proviso that when $R^4$ is —$PO_3R^7R^8$, $R^5$ is other than —$PO_3R^9R^{10}$, wherein "*$^{1-3}$" and "**" represent chiral centers; wherein the subscripts n, m, p and q are each independently an integer from 0 to 6, with the proviso that the sum of p and m is from 0 to 6.

In some embodiments, the compounds of the present invention contain an —O— at X and Y, $R^4$ is $PO_3R^7R^8$, $R^5$ and $R^6$ are H, and the subscripts n, m, p, and q are integers from 0 to 3. In a more preferred embodiment, $R^7$ and $R^8$ are —H. In an even more preferred embodiment, subscript n is 1, subscript m is 2, and subscripts p and q are 0. In yet an even more preferred embodiment, $R_1$, $R_2$, and $R_3$ are tetradecanoyl residues. In a still more preferred embodiment, $*^{1-3}$ are in the R configuration, Y is in the equatorial position, and ** is in the S configuration (N—[(R)-3-tetradecanoyloxytetradecanoyl]-(S)-2-pyrrolidinomethyl 2-deoxy-4-O-phosphono-2-[(R)-3-tetradecanoyloxytetradecanoylamino]-3-O—[(R)-3-tetradecanoyloxytetradecanoyl]-β-D-glucopyranoside and pharmaceutically acceptable salts thereof; RC-553; Formula II).

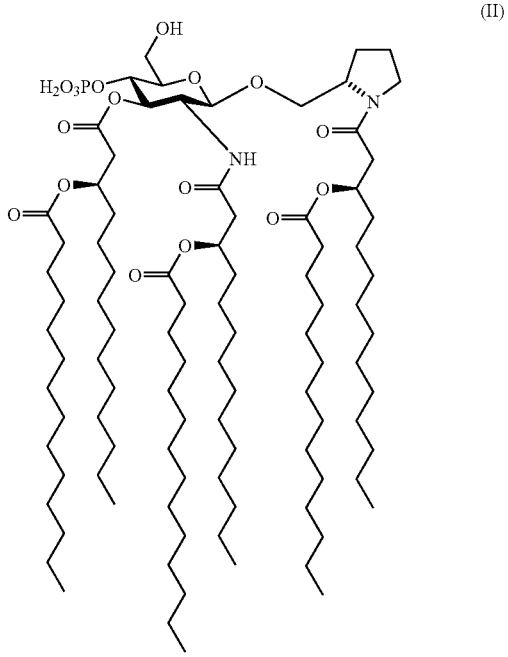

(II)

The present invention also provides compounds which can be used as pharmaceutical compositions containing compounds of the general formula above. The pharmaceutical compositions can be combined with a variety of antigens and in a variety of formulations known to those of skill in the art.

The compounds of the present invention are also useful in methods of inducing an immune response in a subject. The method entails administering a composition containing a therapeutically effective amount of a pharmaceutically acceptable carrier and a compound of the present invention.

The present invention also encompasses methods of treating a mammal suffering from or susceptible to a pathogenic infection, cancer or an autoimmune disorder. The method entails administering to the mammal a therapeutically effective amount of a composition containing a pharmaceutically acceptable carrier and a compound of the present invention.

Still further, the present invention involves a method for treating diseases or conditions ameliorated by nitric oxide production in a subject. The method entails contacting the subject with an effective amount of a compound of the present invention. In some embodiments, the compounds of the present invention can be administered 48 hours prior to, up to, and during ischemia.

DETAILED DESCRIPTION OF THE INVENTION

Definitions

The term "acyl" refers to those groups derived from an organic acid by removal of the hydroxy portion of the acid. Accordingly, acyl is meant to include, for example, acetyl, propionyl, butyryl, decanoyl, pivaloyl, benzoyl and the like.

A "$(C_2-C_{24})$acyl" is an acyl group having from 2 to 24 carbons.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1-C_{10}$ means one to ten carbons). Examples of saturated hydrocarbon radicals include groups such as methyl, ethyl, n-propyl, isopropyl, n-butyl, t-butyl, isobutyl, sec-butyl, cyclohexyl, (cyclohexyl)ethyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Alkyl groups which are limited to hydrocarbon groups are termed "homoalkyl."

A "$(C_1-C_4)$alkyl" is an alkyl group having from 1 to 4 carbons.

The term "alkylene" by itself or as part of another substituent means a divalent radical derived from an alkane, as exemplified by —$CH_2CH_2CH_2CH_2$—, and further includes those groups known as "heteroalkylenes."

The terms "alkoxy," "alkylamino" and "alkylthio" refer to those groups having an alkyl group attached to the remainder of the molecule through an oxygen, nitrogen or sulfur atom, respectively.

The term "$(C_1-C_4)$alkoxy" refers to an alkoxy group having from 1 to 4 carbons.

Each of the above terms (e.g., "alkyl," "acyl") are meant to include both substituted and unsubstituted forms of the indicated radical. Preferred substituents for each type of radical are provided below.

Substituents for the alkyl and acyl radicals can be a variety of groups selected from: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —CN and —NO$_2$ in a number ranging from zero to (2m'+1), where m' is the total number of carbon atoms in such radical. R', R" and R'" each independently refer to hydrogen and unsubstituted ($C_1$-$C_8$) alkyl. When R' and R" are attached to the same nitrogen atom, they can be combined with the nitrogen atom to form a 5-, 6-, or 7-membered ring. For example, —NR'R" is meant to include 1-pyrrolidinyl and 4-morpholinyl. From the above discussion of substituents, one of skill in the art will understand that the term "alkyl" is meant to include groups such as haloalkyl (e.g., —CF$_3$ and —CH$_2$CF$_3$) and the like.

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfiric, hydriodic, or phosphorous acids and the like, as well as the salts derived from relatively nontoxic organic acids like acetic, propionic, isobutyric, oxalic, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al., "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are all intended to be encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are intended to be encompassed within the scope of the present invention.

Introduction

In an effort to improve the safety of vaccines, manufacturers are avoiding whole cell killed vaccines, and producing recombinant or subunit vaccines. In the preparation of these safer vaccines extraneous bacterial or viral components are eliminated, while the minimal structures or epitopes deemed necessary for protective immunity remain. The safety of these vaccines is improved due to the elimination of extraneous bacterial or viral components which often times prove to be toxic and pyrogenic. However, the same components that result in toxicity provide nonspecific immunostimulation that make whole cell vaccines so effective. Without the additional immunostimulation the minimal structures and epitopes comprising recombinant and subunit vaccines are often poorly immunogenic.

A disaccharide molecule derived from the LPS of *Salmonella minnesota* R595, MPL® immunostimulant (Corixa Corp.), has immunostimulant properties. MPL® immunostimulant, Monophosphoryl lipid A, is a structural derivative of lipid A (or LPS) and has an improved therapeutic index relative to lipid A (see U.S. Pat. No. 4,987,237 for the structure of Monophosphoryl lipid A; U.S. Pat. Nos. 4,436,727 and 4,436,728 for description of preparation of Monophosphoryl lipid A). Other useful immunostimulants include 3-de-O-acylated monophosphoryl lipid A (3D-MPL), which is described in U.S. Pat. No. 4,912,094. The compound can be safely administered to humans as doses up to at least 20 µg/kg, although increases in temperature, flu-like symptoms, increasing heart rate and modest decreases in blood pressure can occur in some patients at dose levels of $\geq 10$ µg/kg. Cell culture and animal evaluations confirm MPL® immunostimulant still retains some of the immunostimulatory activity of the parent LPS in that pyrogenicity and the ability to induce pro-inflammatory cytokines such as TNF and IL-8 remain, albeit at higher dose levels. Thus, the need for effective vaccine adjuvants is well recognized. Ideally, these adjuvants will boost the protective immune response without inducing unwanted toxicity and pyrogenicity.

In an effort to obtain an immunostimulant that has low pyrogenicity, synthetic molecules have been prepared which share structural similarities with the MPL® immunostimulant (see U.S. patent application Ser. No. 09/810,915, Filed on Mar. 16, 2001, and the present invention). These novel molecules which are collectively called aminoalkyl glucosaminide phosphates (AGPs), consist of an acylated glucose moiety linked to an acylated aminoalkyl group (Johnson et al. (1999) *Bioorg. Med. Chem. Lett.* 9: 2273-2278; PCT/WO98/50399 and references therein). Each molecule possesses 6 fatty acid tails which is thought to be the optimal number for peak adjuvant activity. The substitution of different chemical moieties within the aminoalkyl structures was designed into the AGPs in anticipation of optimizing stability and solubility properties. Thus the AGPs can be broadly separated into several families based on the structure of their aminoalkyl groups. After initial biological evaluation, it became apparent that the aminoalkyl motifs could dramatically affect the pyrogenic properties of the AGPs (see U.S. patent application Ser. No. 09/810,915 (filed on Mar. 16, 2001), Ser. No. 09/439,839 (now U.S. Pat. No. 6,303,347), Ser. No. 09/074,720 (now U.S. Pat. No. 6,355,257) and U.S. Pat. No. 6,113,918 (which issued from U.S. Ser. No. 08/853,826). As part of the initial screening process of the synthetic adjuvant compounds, rabbit pyrogenicity data was determined. It was noted that several of the compounds did not elicit a fever response when administered i.v. at doses of 10 μg/kg. In general, these same compounds failed to induce detectable levels of inflammatory cytokines TNF-α or IL-1β in an ex vivo cytokine induction assay on human peripheral blood mononuclear cells. Here we report on studies of the adjuvant properties of a class of AGPs which induce minimal activity in both the rabbit pyrogen test and the ex vivo cytokine assay.

Compounds and Compositions

The present invention provides compounds described generally by formula (I):

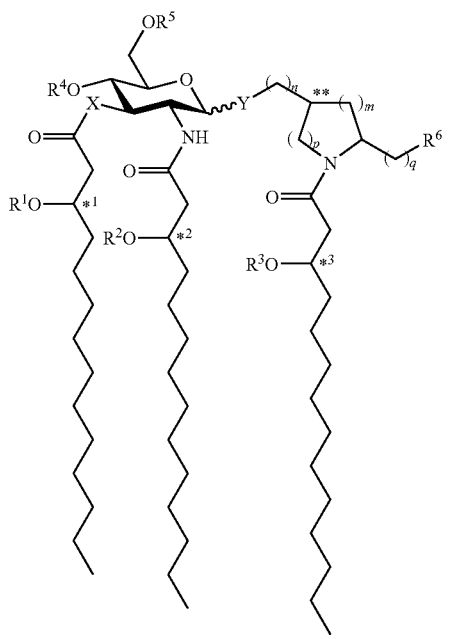

(I)

and pharmaceutically acceptable salts thereof, wherein X is —O— or —NH— and Y is —O— or —S—; $R^1$, $R^2$, and $R^3$ are each independently a ($C_2$-$C_{24}$)acyl group, including saturated, unsaturated and branched acyl groups; $R^4$ is —H or —$PO_3R^7R^8$, wherein $R^7$ and $R^8$ are each independently H or ($C_1$-$C_4$)alkyl; $R^5$ is —H, —$CH_3$ or —$PO_3R^9R^{10}$, wherein $R^9$ and $R^{10}$ are each independently selected from —H and ($C_1$-$C_4$)alkyl; $R^6$ is independently selected from H, OH, ($C_1$-$C_4$) alkoxy, —$PO_3R^{11}R^{12}$, —$OPO_3R^{11}R^{12}$, —$SO_3R^{11}$, —$OSO_3R^{11}$, —$NR^{11}R^{12}$, —$SR^{11}$, —CN, —$NO_2$, —CHO, —$CO_2R^{11}$, and —$CONR^{11}R^{12}$, wherein $R^{11}$ and $R^{12}$ are each independently selected from H and ($C_1$-$C_4$)alkyl; with the proviso that when $R^4$ is —$PO_3R^7R^8$, $R^5$ is other than —$PO_3R^9R^{10}$, wherein "*$^{1-3}$" and "**" represent chiral centers; wherein the subscripts n, m, p and q are each independently an integer from 0 to 6, with the proviso that the sum of p and m is from 0 to 6.

Although the hexopyranoside in Formula I is shown in the gluco configuration, other glycosides are within the scope of the invention. For example glycopyranosides, including other hexopyranosides (e.g., allo, altro, manno, gulo, ido, galacto, talo), are within the scope of the invention.

In the general formula above, the configuration of the 3'-stereogenic centers to which the normal fatty acyl residues are attached, denoted "*$^1$", "*$^2$" and "*$^3$", is R or S, but preferably R. The absolute stereochemistry of the carbon atoms of the cyclic aglycon unit to which $R^6$ and the glucosamine unit are attached, directly or indirectly (denoted "**") can be R or S. In the general formula above, Y can be in the equatorial or axial position, but is preferably equatorial. All stereoisomers, enantiomers, diastereomers and mixtures thereof are considered to be within the scope of the present invention.

In preferred embodiments, of the present invention, X and Y are —O—, $R^4$ is phosphono, $R^5$ and $R^6$ are H, and the subscripts n, m, p, and q are integers of from 0 to 3, and more preferably 0 to 2. Most preferably the integer n is 1, the integer m is 2, and integers p and q are 0. In this preferred embodiment, the compounds of this invention are 2-pyrrolidinomethyl β-D-glucosaminide 4-phosphates having the general formula (III):

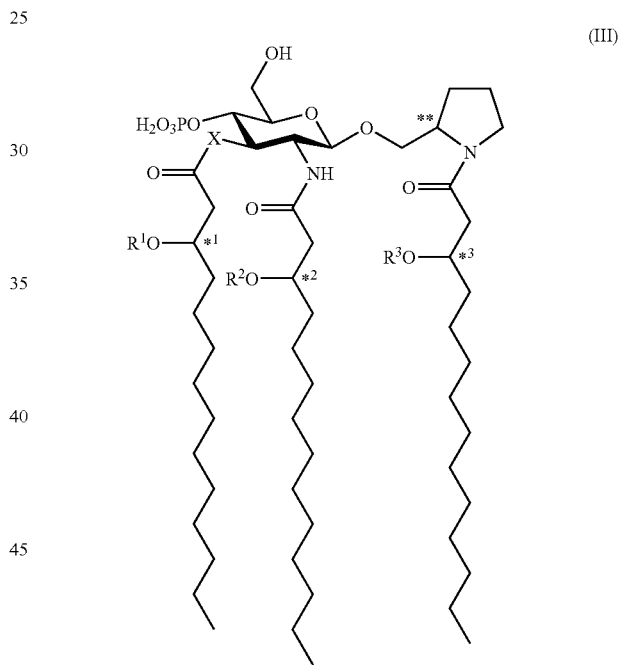

(III)

In the most preferred embodiment of the present invention, $R_1$, $R_2$, and $R_3$ of formula (III) are tetradecanoyl residues and the configuration of the 3'-stereogenic centers ("*$^{1-3}$") to which they are attached is R, Y is in the equatorial position, and the absolute stereochemistry of the pyrrolidine stereogenic center ("**") is S. Specifically, the compound of the most preferred embodiment is N—[(R)-3-tetradecanoyloxytetradecanoyl]-(S)-2-pyrrolidinomethyl 2-deoxy-4-O-phosphono-2-[(R)-3-tetradecanoyloxytetradecanoylamino]-3-O—[(R)-3-tetradecanoyloxytetradecanoyl]-β-D-glucopyranoside and pharmaceutically acceptable salts thereof. This most preferred embodiment is also known as RC-553 and is depicted in formula II:

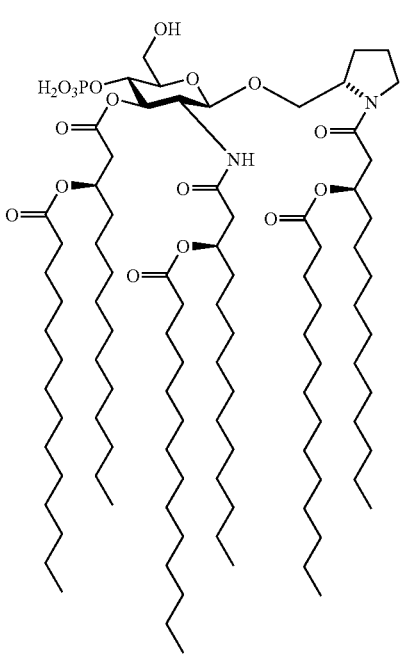

(II)

Preparation of Compounds

The compounds of the present invention can be prepared using methods outlined in Johnson et al., *Bioorg. Med. Chem. Lett.* 9:2273-2278 (1999) and PCT/WO98/50399 and references therein. In general, the synthetic methods described in the above-noted references are broadly applicable to the preparation of compounds having different acyl groups and substitutions. One of skill in the art will appreciate that the convergent methods described therein can be modified to use alternate acylating agents, or can be initiated with commercially available materials having appropriate acyl groups attached.

Evaluation of Compounds

The compounds provided herein can be evaluated in a variety of assay formats to select a compound having a suitable pharmacophoric profile. For example, U.S. Pat. No. 6,013,640 describes animal models suitable for evaluating cardioprotective effects of compounds described herein. The examples below also provide assays for evaluating pyrogenicity of the subject compounds, and further assays for evaluating the proinflammatory effects of the compounds.

The present invention further provides pharmaceutical compositions comprising the compounds provided herein in admixture with one or more pharmaceutically acceptable carriers. Suitable carriers will depend on the condition being treated along with the route of administration. Accordingly, a discussion of the carriers is provided below in conjunction with the methods of use.

Pharmaceutical Compositions and Their Uses

In one embodiment, the present invention provides pharmaceutical compositions containing a compound of the present invention and a pharmaceutically acceptable carrier. The compound is present in a therapeutically effective amount, which the amount of compound required to achieve the desired effect in terms of treating a disease, condition, or achieving a biological occurrence. The pharmaceutical compositions can act as an adjuvant when co-administered with an antigen.

Thus, the adjuvant systems of the invention are particularly advantageous in making and using vaccine and other immunostimulant compositions to treat or prevent diseases, such inducing active immunity towards antigens in mammals, preferably in humans. Vaccine preparation is a well developed art and general guidance in the preparation and formulation of vaccines is readily available from any of a variety of sources. One such example is New Trends and Developments in Vaccines, edited by Voller et al., University Park Press, Baltimore, Md., U.S.A. 1978.

In one illustrative embodiment, the antigen in a vaccine composition of the invention is a peptide, polypeptide, or immunogenic portion thereof. An "immunogenic portion," as used herein is a portion of a protein that is recognized (i.e., specifically bound) by a B-cell and/or T-cell surface antigen receptor. Such immunogenic portions generally comprise at least 5 amino acid residues, more preferably at least 10, and still more preferably at least 20 amino acid residues of an antigenic protein or a variant thereof.

Immunogenic portions of antigen polypeptides may generally be identified using well known techniques, such as those summarized in Paul, *Fundamental Immunology*, 3rd ed., 243-247 (Raven Press, 1993) and references cited therein. Such techniques include screening polypeptides for the ability to react with antigen-specific antibodies, antisera and/or T-cell lines or clones. As used herein, antisera and antibodies are "antigen-specific" if they specifically bind to an antigen (i.e., they react with the protein in an ELISA or other immunoassay, and do not react detectably with unrelated proteins). Such antisera and antibodies may be prepared as described herein, and using well known techniques. An immunogenic portion of a protein is a portion that reacts with such antisera and/or T-cells at a level that is not substantially less than the reactivity of the full length polypeptide (e.g., in an ELISA and/or T-cell reactivity assay). Such immunogenic portions may react within such assays at a level that is similar to or greater than the reactivity of the full length polypeptide. Such screens may generally be performed using methods well known to those of ordinary skill in the art, such as those described in Harlow and Lane, *Antibodies: A Laboratory Manual*, Cold Spring Harbor Laboratory, 1988. For example, a polypeptide may be immobilized on a solid support and contacted with patient sera to allow binding of antibodies within the sera to the immobilized polypeptide. Unbound sera may then be removed and bound antibodies detected using, for example, $^{125}$I-labeled Protein A.

Peptide and polypeptide antigens are prepared using any of a variety of well-known techniques. Recombinant polypeptides encoded by DNA sequences may be readily prepared from isolated DNA sequences using any of a variety of expression vectors known to those of ordinary skill in the art. Expression may be achieved in any appropriate host cell that has been transformed or transfected with an expression vector containing a DNA molecule that encodes a recombinant polypeptide. Suitable host cells include prokaryotes, yeast, and higher eukaryotic cells, such as mammalian cells and plant cells. Preferably, the host cells employed are *E. coli*, yeast or a mammalian cell line such as COS or CHO.

Portions and other variants of a protein antigen having less than about 100 amino acids, and generally less than about 50 amino acids, may also be generated by synthetic means, using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85:2149-2146, 1963.

Equipment for automated synthesis of polypeptides is commercially available from suppliers such as Perkin Elmer/Applied BioSystems Division (Foster City, Calif.), and may be operated according to the manufacturer's instructions.

Within certain specific embodiments, a polypeptide antigen used in the vaccine compositions of the invention may be a fusion protein that comprises two or more distinct polypeptides. A fusion partner may, for example, assist in providing T helper epitopes (an immunological fusion partner), preferably T helper epitopes recognized by humans, or may assist in expressing the protein (an expression enhancer) at higher yields than the native recombinant protein. Certain preferred fusion partners are both immunological and expression enhancing fusion partners. Other fusion partners may be selected so as to increase the solubility of the protein or to enable the protein to be targeted to desired intracellular compartments. Still further fusion partners include affinity tags, which facilitate purification of the protein.

Fusion proteins may generally be prepared using standard techniques, including chemical conjugation. Preferably, a fusion protein is expressed as a recombinant protein, allowing the production of increased levels, relative to a non-fused protein, in an expression system. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion protein that retains the biological activity of both component polypeptides.

A peptide linker sequence may be employed to separate the first and second polypeptide components by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39-46, 1985; Murphy et al., *Proc. Natl. Acad. Sci. USA* 83:8258-8262, 1986; U.S. Pat. Nos. 4,935,233 and 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

Within preferred embodiments, an immunological fusion partner is derived from protein D, a surface protein of the gram-negative bacterium *Haemophilus influenza* B (WO 91/18926). Preferably, a protein D derivative comprises approximately the first third of the protein (e.g., the first N-terminal 100-110 amino acids), and a protein D derivative may be lipidated. Within certain preferred embodiments, the first 109 residues of a Lipoprotein D fusion partner is included on the N-terminus to provide the polypeptide with additional exogenous T-cell epitopes and to increase the expression level in *E. coli* (thus functioning as an expression enhancer). The lipid tail ensures optimal presentation of the antigen to antigen presenting cells. Other fusion partners include the non-structural protein from influenzae virus, NS1 (hemagglutinin). Typically, the N-terminal 81 amino acids are used, although different fragments that include T-helper epitopes may be used.

In another embodiment, the immunological fusion partner is the protein known as LYTA, or a portion thereof (preferably a C-terminal portion). LYTA is derived from *Streptococcus pneumoniae*, which synthesizes an N-acetyl-L-alanine amidase known as amidase LYTA (encoded by the LytA gene; *Gene* 43:265-292, 1986). LYTA is an autolysin that specifically degrades certain bonds in the peptidoglycan backbone. The C-terminal domain of the LYTA protein is responsible for the affinity to the choline or to some choline analogues such as DEAE. This property has been exploited for the development of *E. coli* C-LYTA expressing plasmids useful for expression of fusion proteins. Purification of hybrid proteins containing the C-LYTA fragment at the amino terminus has been described (see *Biotechnology* 10:795-798, 1992). Within a preferred embodiment, a repeat portion of LYTA may be incorporated into a fusion protein. A repeat portion is found in the C-terminal region starting at residue 178. A particularly preferred repeat portion incorporates residues 188-305.

In another embodiment of the invention, the adjuvant system described herein is used in the preparation of DNA-based vaccine compositions. Illustrative vaccines of this type contain DNA encoding one or more polypeptide antigens, such that the antigen is generated in situ. The DNA may be present within any of a variety of delivery systems known to those of ordinary skill in the art, including nucleic acid expression systems, bacteria and viral expression systems. Numerous gene delivery techniques are well known in the art, such as those described by Rolland, *Crit. Rev. Therap. Drug Carrier Systems* 15:143-198, 1998, and references cited therein. Appropriate nucleic acid expression systems contain the necessary DNA sequences for expression in the patient (such as a suitable promoter and terminating signal). Bacterial delivery systems involve the administration of a bacterium (such as *Bacillus-Calmette-Guerrin*) that expresses an immunogenic portion of the polypeptide on its cell surface or secretes such an epitope. In one preferred embodiment, the DNA is introduced using a viral expression system (e.g., vaccinia or other pox virus, retrovirus, or adenovirus), which typically involves the use of a non-pathogenic (defective), replication competent virus. Illustrative systems are disclosed, for example, in Fisher-Hoch et al., *Proc. Natl. Acad. Sci. USA* 86:317-321, 1989; Flexner et al., *Ann. N.Y. Acad. Sci.* 569:86-103, 1989; Flexner et al., *Vaccine* 8:17-21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, *Biotechniques* 6:616-627, 1988; Rosenfeld et al., *Science* 252:431-434, 1991; Kolls et al., *Proc. Natl. Acad. Sci. USA* 91:215-219, 1994; Kass-Eisler et al., *Proc. Natl. Acad. Sci. USA* 90:11498-11502, 1993; Guzman et al., *Circulation* 88:2838-2848, 1993; and Guzman et al., *Cir. Res.* 73:1202-1207, 1993. Techniques for incorporating DNA into such expression systems are well known to those of ordinary skill in the art.

Alternatively, the DNA may be "naked," as described, for example, in Ulmer et al., *Science* 259:1745-1749, 1993 and reviewed by Cohen, *Science* 259:1691-1692, 1993. The uptake of naked DNA may be increased by coating the DNA onto biodegradable beads that are efficiently transported into the cells. It will be apparent that a vaccine may comprise both a polynucleotide and a polypeptide component if desired.

Moreover, it will be apparent that a vaccine may contain pharmaceutically acceptable salts of the desired polynucleotide, polypeptide and/or carbohydrate antigens. For example, such salts may be prepared from pharmaceutically acceptable non-toxic bases, including organic bases (e.g., salts of primary, secondary and tertiary amines and basic amino acids) and inorganic bases (e.g., sodium, potassium, lithium, ammonium, calcium and magnesium salts).

The adjuvant system of the present invention exhibits strong adjuvant effects when administered over a wide range of dosages and a wide range of ratios.

The amount of antigen in each vaccine dose is generally selected as an amount which induces an immunoprotective response without significant adverse side effects in typical vaccines. Such amount will vary depending upon which specific immunogen is employed and how it is presented. Generally, it is expected that each dose will comprise about 1-1000 µg of protein, most typically about 2-100 µg, preferably about 5-50 µg. Of course, the dosage administered may be dependent upon the age, weight, kind of concurrent treatment, if any, and nature of the antigen administered.

The immunogenic activity of a given amount of a vaccine composition of the present invention can be readily determined, for example by monitoring the increase in titer of antibody against the antigen used in the vaccine composition (Dalsgaard, K. *Acta Veterinia Scandinavica* 69:1-40 (1978)). Another common method involves injecting CD-1 mice intradermally with various amounts of a vaccine composition, later harvesting sera from the mice and testing for anti-immunogen antibody, e.g., by ELISA. These and other similar approaches will be apparent to the skilled artisan.

The antigen can be derived and/or isolated from essentially any desired source depending on the infectious disease, autoimmune disease, condition, cancer, pathogen, or a disease that is to be treated with a given vaccine composition. By way of illustration, the antigens can be derived from viral sources, such as influenza virus, feline leukemia virus, feline immunodeficiency virus, Human HIV-1, HIV-2, Herpes Simplex virus type 2, Human cytomegalovirus, Hepatitis A, B, C or E, Respiratory Syncytial virus, human papilloma virus rabies, measles, or hoof and mouth disease viruses. Illustrative antigens can also be derived from bacterial sources, such as anthrax, diphtheria, Lyme disease, malaria, tuberculosis, Leishmaniasis, *T. cruzi, Ehrlichia, Candida* etc., or from protozoans such as *Babeosis bovis* or *Plasmodium*. The antigen(s) will typically be comprised of natural or synthetic amino acids, e.g., in the form of peptides, polypeptides, or proteins, can be comprised of polysaccharides, or can be mixtures thereof. Illustrative antigens can be isolated from natural sources, synthesized by means of solid phase synthesis, or can be obtained by way of recombinant DNA techniques.

In another embodiment, tumor antigens are used in the vaccine compositions of the present invention for the prophylaxis and/or therapy of cancer. Cancer cells often have distinctive antigens on their surfaces, such as truncated epidermal growth factor, folate binding protein, epithelial mucins, melanoferrin, carcinoembryonic antigen, prostate-specific membrane antigen, HER2-neu, which are candidates for use in therapeutic cancer vaccines. Because tumor antigens are normal or related to normal components of the body, the immune system often fails to mount an effective immune response against those antigens to destroy the tumor cells. To achieve such a response, the adjuvant systems described herein can be utilized. As a result, exogenous proteins can enter the pathway for processing endogenous antigens, leading to the production of cytolytic or cytotoxic T cells (CTL). This adjuvant effect facilitates the production of antigen specific CTLs which seek and destroy those tumor cells carrying on their surface the tumor antigen(s) used for immunization. Illustrative cancer types for which this approach can be used include prostate, colon, breast, ovarian, pancreatic, brain, head and neck, melanoma, leukemia, lymphoma, etc.

In another embodiment of the invention, the adjuvant system of the present invention can be administered alone, i.e., without a co-administered antigen, to potentiate the immune system for treatment of chronic infectious diseases, especially in immune compromised patients. Illustrative examples of infectious diseases for which this approach may be employed for therapeutic or prophylactic treatment can be found in U.S. Pat. No. 5,508,310. Potentiation of the immune system in this way can also be useful as a preventative measure to limit the risks of nosocomial and/or post-surgery infections.

In another embodiment, the antigen present in the vaccine compositions is not a foreign antigen, rather it is a self antigen, e.g., the vaccine composition is directed toward an autoimmune disease such as type 1 diabetes, conventional organ-specific autoimmune diseases, neurological diseases, rheumatic diseases, psoriasis, connective tissue diseases, autoimmune cytopenias, and other autoimmune diseases. Such conventional organ specific autoimmunity may include thyroiditis (Graves+Hashimoto's), gastritis, adrenalitis (Addison's), ovaritis, primary biliary cirrhosis, myasthenia gravis, gonadal failure, hypoparathyroidism, alopecia, malabsorption syndrome, pernicious anemia, hepatitis, anti-receptor antibody diseases and vitiligo. Such neurological diseases may include schizophrenia, Alzheimer's disease, depression, hypopituitarism, diabetes insipidus, sicca syndrome and multiple sclerosis. Such rheumatic diseases/connective tissue diseases may include rheumatoid arthritis, systemic lupus erythematous (SLE) or Lupus, scleroderma, polymyositis, inflammatory bowel disease, dermatomyositis, ulcerative colitis, Crohn's disease, vasculitis, psoriatic arthritis, exfoliative psoriatic dermatitis, pemphigus vulgaris, Sjogren's syndrome. Other autoimmune related diseases may include autoimmune uvoretinitis, glomerulonephritis, post myocardial infarction cardiotomy syndrome, pulmonary hemosiderosis, amyloidosis, sarcoidosis, aphthous stomatitis, and other immune related diseases, as presented herein and known in the related arts.

While any suitable carrier known to those of ordinary skill in the art may be employed in the vaccine compositions of this invention, the type of carrier will typically vary depending on the desired mode of administration. Compositions of the present invention may be formulated for any appropriate manner of administration, including for example, topical, oral, nasal, intravenous, intracranial, intraperitoneal, intradermal, subcutaneous or intramuscular administration. For parenteral administration, such as subcutaneous injection, the carrier will often comprise water, saline, alcohol, a fat, a wax or a buffer. For oral administration, the above carriers are often used, or a solid carrier such as mannitol, lactose, starch, magnesium stearate, sodium saccharine, talcum, cellulose, glucose, sucrose, and magnesium carbonate, can also be employed. Biodegradable microspheres (e.g., polylactate polyglycolate) may also be employed as carriers for the compositions of this invention. Suitable biodegradable microspheres are disclosed, for example, in U.S. Pat. Nos. 4,897,268; 5,075,109; 5,928,647; 5,811,128; 5,820,883; 5,853,763; 5,814,344 and 5,942,252, the disclosures of which are incorporated herein by reference in their entireties. Modified hepatitis B core protein carrier systems are also suitable, such as those described in WO/99 40934, and references cited therein, all incorporated herein by reference. One can also employ a carrier comprising particulate-protein complexes, such as those described in U.S. Pat. No. 5,928,647, the disclosure of which is incorporated herein by reference in its entirety, which are capable of inducing a class I-restricted cytotoxic T lymphocyte responses in a host.

In one illustrative embodiment, the vaccine formulations are administered to the mucosae, in particular to the oral cavity, and preferably to a sublingual site, for eliciting an immune response. Oral cavity administration may be preferred in many instances over traditional parenteral delivery due to the ease and convenience offered by noninvasive administration techniques. Moreover, this approach further provides a means for eliciting mucosal immunity, which can often be difficult to achieve with traditional parenteral delivery, and which can provide protection from airborne pathogens and/or allergens. An additional advantage of oral cavity administration is that patient compliance may be improved with sublingual vaccine delivery, especially for pediatric applications, or for applications traditionally requiring numerous injections over a prolonged period of time, such as with allergy desensitization therapies.

The vaccine compositions can also comprise buffers (e.g., neutral buffered saline, phosphate buffered saline or phosphate buffers w/o saline), carbohydrates (e.g., glucose, mannose, sucrose or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents and/or preservatives. Alternatively, compositions of the present invention may be formulated as a lyophilizate. The compositions can also be encapsulated within liposomes using well known technology.

Therefore, in one embodiment, the vaccine compositions are aqueous formulations comprising an effective amount of one or more surfactants. For example, the composition can be in the form of a micellar dispersion comprising at least one suitable surfactant, e.g., a phospholipid surfactant. Illustrative examples of phospholipids include diacyl phosphatidyl glycerols, such as dimyristoyl phosphatidyl glycerol (DPMG), dipalmitoyl phosphatidyl glycerol (DPPG), and distearoyl phosphatidyl glycerol (DSPG), diacyl phosphatidyl cholines, such as dimyristoyl phosphatidylcholine (DPMC), dipalmitoyl phosphatidylcholine (DPPC), and distearoyl phosphatidylcholine (DSPC); diacyl phosphatidic acids, such as dimyristoyl phosphatidic acid (DPMA), dipalmitoyl phosphatidic acid (DPPA), and distearoyl phosphatidic acid (DSPA); and diacyl phosphatidyl ethanolamines such as dimyristoyl phosphatidyl ethanolamine (DPME), dipalmitoyl phosphatidyl ethanolamine (DPPE) and distearoyl phosphatidyl ethanolamine (DSPE).

Typically, a surfactant:adjuvant molar ratio in an aqueous formulation will be from about 10:1 to about 1:10, more typically from about 5:1 to about 1:5, however any effective amount of surfactant may be used in an aqueous formulation to best suit the specific objectives of interest.

In another embodiment, the composition is an emulsion, such as a water-in-oil emulsion or an oil-in water emulsion. Such emulsions are generally well known to those skilled in this art.

The adjuvant system of the present invention can be employed as the sole adjuvant system, or alternatively, can be administered together with other adjuvants or immunoeffectors. By way of illustration, such adjuvants can include oil-based adjuvants (for example, Freund's Complete and Incomplete), liposomes, mineral salts (for example, AlK$(SO_4)_2$, AlNa$(SO_4)_2$, AlNH$_4$(SO$_4$), silica, alum, Al(OH)$_3$, Ca$_3$(PO$_4$)$_2$, kaolin, and carbon), polynucleotides (for example, poly IC and poly AU acids), polymers (for example, non-ionic block polymers, polyphosphazenes, cyanoacrylates, polymerase-(DL-lactide-co-glycoside), among others, and certain natural substances (for example, lipid A and its derivatives, wax D from *Mycobacterium tuberculosis*, as well as substances found in *Corynebacterium parvum, Bordetella pertussis*, and members of the genus *Brucella*), bovine serum albumin, diphtheria toxoid, tetanus toxoid, edestin, keyhole-limpet hemocyanin, Pseudomonal Toxin A, choleragenoid, cholera toxin, pertussis toxin, viral proteins, and eukaryotic proteins such as interferons, interleukins, or tumor necrosis factor. Such proteins may be obtained from natural or recombinant sources according to methods well known to those skilled in the art. When obtained from recombinant sources, the adjuvant may comprise a protein fragment comprising at least the immunostimulatory portion of the molecule. Other known immunostimulatory macromolecules which can be used in the practice of the invention include, but are not limited to, polysaccharides, tRNA, non-metabolizable synthetic polymers such as polyvinylamine, polymethacrylic acid, polyvinylpyrrolidone, mixed polycondensates (with relatively high molecular weight) of 4',4-diaminodiphenyl-methane-3,3'-dicarboxylic acid and 4-nitro-2-aminobenzoic acid (See Sela, M., Science 166:1365-1374 (1969)) or glycolipids, lipids or carbohydrates.

In one embodiment, the adjuvant system is preferably designed to induce an immune response predominantly of the Th1 type. High levels of Th1-type cytokines (e.g., IFN-γ, TNFα, IL-2 and IL-12) tend to favor the induction of cell mediated immune responses to an administered antigen. In contrast, high levels of Th2-type cytokines (e.g., IL-4, IL-5, IL-6 and IL-10) tend to favor the induction of humoral immune responses. Following application of a vaccine as provided herein, a patient will support an immune response that includes Th1- and Th2-type responses. Within a preferred embodiment, in which a response is predominantly Th1-type, the level of Th1-type cytokines will increase to a greater extent than the level of Th2-type cytokines. The levels of these cytokines may be readily assessed using standard assays. For a review of the families of cytokines, see Mosmann and Coffman, *Ann. Rev. Immunol.* 7:145-173, 1989.

For example, additional adjuvants for use in eliciting a predominantly Th1-type response include, for example, a combination of monophosphoryl lipid A, such as 3-de-O-acylated monophosphoryl lipid A (3D-MPL), together with an aluminum salt. MPL adjuvants are available from Corixa Corporation (Seattle, Wash.; see U.S. Pat. Nos. 4,436,727; 4,877,611; 4,866,034 and 4,912,094). CpG-containing oligonucleotides (in which the CpG dinucleotide is unmethylated) also induce a predominantly Th1 response. Such oligonucleotides are well known and are described, for example, in WO 96/02555, WO 99/33488 and U.S. Pat. Nos. 6,008,200 and 5,856,462. Immunostimulatory DNA sequences are also described, for example, by Sato et al., *Science* 273:352, 1996. Other illustrative adjuvants that can be included in the vaccine compositions include Montanide ISA 720 (Seppic, France), SAF (Chiron, Calif., United States), ISCOMS (CSL), MF-59 (Chiron), Detox™ adjuvant (Corixa, Hamilton, Mont.).

The compositions described herein may be administered as part of a sustained release formulation (i.e., a formulation such as a capsule, sponge or gel (composed of polysaccharides, for example) that effects a slow release of compound following administration). Such formulations may generally be prepared using well known technology (see, e.g., Coombes et al., *Vaccine* 14:1429-1438, 1996) and administered by, for example, oral, rectal or subcutaneous implantation, or by implantation at the desired target site. Sustained-release formulations may contain a polypeptide, polynucleotide or antibody dispersed in a carrier matrix and/or contained within a reservoir surrounded by a rate controlling membrane. Carriers for use within such formulations are biocompatible, and may also be biodegradable; preferably the formulation provides a relatively constant level of active component release. Such carriers include microparticles of poly(lactide-co-glycolide), polyacrylate, latex, starch, cellulose, dextran and the like. Other delayed-release carriers include supramolecular biovectors, which comprise a non-liquid hydrophilic core (e.g., a cross-linked polysaccharide or oligosaccharide) and, optionally, an external layer comprising an amphiphilic compound, such as a phospholipid (see e.g., U.S. Pat. No. 5,151,254 and PCT applications WO 94/20078, WO/94/23701 and WO 96/06638). The amount of active compound contained within a sustained release formulation will vary depending upon the site of implantation, the rate and expected duration of release and the nature of the condition to be treated or prevented.

Any of a variety of known delivery vehicles may be employed within pharmaceutical compositions and vaccines to facilitate production of an antigen-specific immune response that targets cells. Delivery vehicles include antigen presenting cells (APCs), such as dendritic cells, macrophages, B cells, monocytes and other cells that may be engineered to be efficient APCs. Such cells may, but need not, be genetically modified to increase the capacity for presenting the antigen, to improve activation and/or maintenance of the T cell response, to have anti-target effects per se and/or to be immunologically compatible with the receiver (i.e., matched HLA haplotype). APCs may generally be isolated from any of a variety of biological fluids and organs, including tumor and peritumoral tissues, and may be autologous, allogeneic, syngeneic or xenogeneic cells.

Certain preferred embodiments of the present invention use dendritic cells or progenitors thereof as antigen-presenting cells. Dendritic cells are highly potent APCs (Banchereau and Steinman, *Nature* 392:245-251, 1998) and have been shown to be effective as a physiological adjuvant for eliciting prophylactic or therapeutic antitumor immunity (see Timmerman and Levy, *Ann. Rev. Med.* 50:507-529, 1999). In general, dendritic cells may be identified based on their typical shape (stellate in situ, with marked cytoplasmic processes (dendrites) visible in vitro), their ability to take up, process and present antigens with high efficiency and their ability to activate naïve T cell responses. Dendritic cells may, of course, be engineered to express specific cell-surface receptors or ligands that are not commonly found on dendritic cells in vivo or ex vivo, and such modified dendritic cells are contemplated by the present invention. As an alternative to dendritic cells, secreted vesicles antigen-loaded dendritic cells (called exosomes) may be used within a vaccine (see Zitvogel et al., *Nature Med.* 4:594-600, 1998).

Dendritic cells and progenitors may be obtained from peripheral blood, bone marrow, tumor-infiltrating cells, peritumoral tissues-infiltrating cells, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNFα to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNFα, CD40 ligand, LPS, flt3 ligand and/or other compound(s) that induce differentiation, maturation and proliferation of dendritic cells.

Dendritic cells are conveniently categorized as "immature" and "mature" cells, which allows a simple way to discriminate between two well characterized phenotypes. However, this nomenclature should not be construed to exclude all possible intermediate stages of differentiation. Immature dendritic cells are characterized as APC with a high capacity for antigen uptake and processing, which correlates with the high expression of Fcγ receptor and mannose receptor. The mature phenotype is typically characterized by a lower expression of these markers, but a high expression of cell surface molecules responsible for T cell activation such as class I and class II MHC, adhesion molecules (e.g., CD54 and CD11) and costimulatory molecules (e.g., CD40, CD80, CD86 and 4-1BB).

APCs may generally be transfected with a polynucleotide encoding an antigen polypeptide (or portion or other variant thereof) such that the antigen polypeptide, or an immunogenic portion thereof, is expressed on the cell surface. Such transfection may take place ex vivo, and a composition or vaccine comprising such transfected cells, and the adjuvants described herein, may then be used for therapeutic purposes. Alternatively, a gene delivery vehicle that targets a dendritic or other antigen presenting cell may be administered to a patient, resulting in transfection that occurs in vivo. In vivo and ex vivo transfection of dendritic cells, for example, may generally be performed using any methods known in the art, such as those described in WO 97/24447, or the gene gun approach described by Mahvi et al., *Immunology and cell Biology* 75:456-460, 1997. Antigen loading of dendritic cells may be achieved by incubating dendritic cells or progenitor cells with the antigen polypeptide, DNA (naked or within a plasmid vector) or RNA; or with antigen-expressing recombinant bacterium or viruses (e.g., vaccinia, fowlpox, adenovirus or lentivirus vectors). Prior to loading, the polypeptide may be covalently conjugated to an immunological partner that provides T cell help (e.g., a carrier molecule). Alternatively, a dendritic cell may be pulsed with a non-conjugated immunological partner, separately or in the presence of the polypeptide.

Treatment of Nitric Oxide Related Disorders

In one aspect, the present invention provides methods for treating diseases or conditions mediated by nitric oxide, particularly ischemia and reperfusion injury. The methods comprise administering to a subject in need of such treatment an effective amount of a compound of the present invention. It is generally agreed that inducers of iNOS gene transcription and protein synthesis are proinflammatory and consequently somewhat "toxic" or poorly tolerated in animals and humans. Endotoxin (LPS) and proinflammatory cytokines such as IL-1, TNF-α and IFN-γ are known inducers of iNOS. All are inherently toxic and capable of inducing a systemic inflammatory response, adult respiratory distress syndrome, multiple organ failure and cardiovascular collapse when administered to animals.

Investigation of the cardioprotective activity of MPL® immunostimulant demonstrated that induction of nitric oxide synthases (iNOS) is important in the delayed cardioprotective effect of the compound. Additionally, nitric oxide (NO) signaling, presumably through constitutive pools of NOS, is important in the acute cardioprotective effect of the compound. In view of the residual endotoxic-like activity of MPL® immunostimulant, it is not surprising that the compound could be capable of inducing nitric oxide signaling.

Still further, nitric oxide signaling has been suggested as a potential pathway by which ischemic preconditioning elicits cardioprotection. This observation in combination with the fact that nitric oxide donors are cardioprotective provides further support for the NOS/NO pathway as the route for MPL® immunostimulant cardioprotection.

The compounds of the present invention, including RC-553, are useful in methods for treating diseases or conditions modulated or ameliorated by nitric oxide, particularly ischemia and reperfusion injury (see, U.S. patent application Ser. No.: 09/808,669, filed Mar. 14, 2001, now U.S. Pat. No. 6,699,846, for a description of the cardioprotective properties of aminoalkyl glucosaminide phosphates and methods for assaying cardioprotective properties).

EXAMPLES

The following examples are offered to illustrate, but not to limit the claimed invention.

Example 1

Preparation of RC-553

Preparation of N—[(R)-3-Tetradecanoyloxytetradecanoyl]-(S)-2-pyrrolidinomethyl 2-Deoxy-4-O-phosphono-2-[(R)-3-tetradecanoyloxytetradecanoylamino]-3-O—[(R)-3-tetradecanoyloxytetradecanoyl]-β-D-glucopyranoside Triethylammonium Salt (formula (I), $R_1=R_2=R_3=C_{13}H_{27}CO$, X=Y=O, n=1, m=2, p=q=0, $R_5=R_6=H$, $R_4=PO_3H_2$; formula (II) $R_1=R_2=R_3=C_{13}H_{27}CO$); RC-553.

(1) To a solution of 2-deoxy-4-O-diphenylphosphono-3-O—[(R)-3-tetradecanoyloxytetradecanoyl]-6-O-(2,2,2-trichloro-1,1-dimethylethoxycarbonyl)-2-(2,2,2-trichloroethoxycarbonylamino)-β-D-glucopyranosyl bromide (1.05 g, 0.81 mmol) in dry 1,2-dichloroethane (10 mL) were added 4 Å molecular sieves (0.5 g), anhydrous $CaSO_4$ (2.2 g, 16 mmol), and N—[(R)-3-tetradecanoyloxytetradecanoyl]-(S)-2-pyrrolidinomethanol (0.40 g, 0.75 mmol). The resulting mixture was stirred for 1 h at room temperature, treated with $Hg(CN)_2$ (1.02 g, 4.05 mmol), and heated to reflux for 16 h in the dark. The cooled reaction mixture was diluted with $CH_2Cl_2$ and filtered. The filtrate was washed with 1 N aq KI, dried ($Na_2SO_4$), and concentrated. Flash chromatography on silica gel (gradient elution, 15→20% EtOAc/hexanes) afforded 0.605 g (43%) of N—[(R)-3-tetradecanoyloxytetradecanoyl]-(S)-2-pyrrolidinomethyl 2-deoxy-4-O-diphenylphosphono-3-O—[(R)-3-tetradecanoyloxytetradecanoyl]-6-O-(2,2,2-trichloro-1,1-dimethylethoxycarbonyl)-2-(2,2,2-trichloroethoxycarbonylamino)-β-D-glucopyranoside as an amorphous solid.

(2) A solution of the compound prepared in (1) above (0.50 g, 0.29 mmol) in AcOH (10 mL) at 60° C. was treated with zinc dust (0.98 g, 15 mmol) in three equal portions over a 1-h period. The cooled reaction mixture was sonicated, filtered through a pad of Celite, and concentrated. The resulting residue was partitioned between $CH_2Cl_2$ and saturated aq $NaHCO_3$, and the layers were separated. The organic layer was dried ($Na_2SO_4$) and concentrated. A solution of the crude amino alcohol obtained and (R)-3-tetradecanoyloxytetradecanoic acid (0.155 g, 0.34 mmol) in $CH_2Cl_2$ (3.5 mL) was stirred with powdered 4 Å molecular sieves (0.25 g) for 0.5 h and then treated with 2-ethoxy-1-ethoxycarbonyl-1,2-dihydroquinoline (0.11 g, 0.44 mmol). The resulting mixture was stirred at room temperature for 8 h, filtered through Celite, and concentrated. Flash chromatography on silica gel with 50% EtOAc/hexanes gave 0.355 g (68%) of N—[(R)-3-tetradecanoyloxytetradecanoyl]-(S)-2-pyrrolidinomethyl 2-deoxy-4-O-diphenylphosphono-2-[(R)-3-tetradecanoyloxytetradecanoylamino]-3-O—[(R)-3-tetradecanoyloxytetradecanoyl]-β-D-glucopyranoside as a colorless syrup.

(3) A solution of the compound prepared in (2) above (0.300 g, 0.166 mmol) in a mixture of AcOH (1 μL) and tetrahydrofuran (9 mL) was hydrogenated in the presence of $PtO_2$ (0.15 g) at room temperature and 70 psig for 18 h. The reaction mixture was diluted with 2:1 $CHCl_3$—MeOH (50 mL) and sonicated briefly. The catalyst was collected and washed with 2:1 $CHCl_3$—MeOH and the combined filtrate and washings were concentrated. Flash chromatography on silica gel with $CHCl_3$—MeOH—$H_2O$—$Et_3N$ (90:10:0.5:0.5) gave partially purified product which was dissolved in ice-cold 2:1 $CHCl_3$—MeOH (30 mL) and washed with ice-cold 0.1 N aq HCl (12 mL). The organic phase was filtered and lyophilized from 2% aq $Et_3N$ (5 mL, pyrogen-free) to give 0.228 g (79%) of N—[(R)-3-tetradecanoyloxytetradecanoyl]-(S)-2-pyrrolidinomethyl 2-deoxy-4-O-phosphono-2-[(R)-3-tetradecanoyloxytetradecanoylamino]-3-O—[(R)-3-tetradecanoyloxytetradecanoyl]-β-D-glucopyranoside triethylammonium salt as a colorless powder: mp 67-70° C.; IR (film) 3306, 2955, 2923, 2853, 1736, 1732, 1644, 1548, 1466, 1378, 1245, 1177, 1110, 1053, 844 $cm^{-1}$; $^1H$ NMR ($CDCl_3$—$CD_3OD$) δ 0.88 (m, 18H), 1.0-1.2.05 (mH), 2.20-2.70 (m, 12H), 3.06 (q, 6H, J=7.2 Hz), 3.3-325 (mH), 4.52 (d, 1H, J=8 Hz), 5.05-5.28 (m, 4H), 7.44 (d, 1H, J=9 Hz); $^{13}C$ NMR ($CDCl_3$) δ 173.3, 173.0, 170.3, 169.6, 168.6, 101.8, 100.4, 75.8, 72.5, 72.4, 70.9, 70.8, 70.3, 70.2, 69.9, 69.3, 67.9, 66.6, 56.5, 56.3, 54.5, 47.4, 45.8, 44.6, 41.4, 41.0, 39.7, 39.2, 39.0, 34.5, 34.3, 34.1, 32.0, 29.7, 29.4, 28.1, 27.3, 25.7, 25.3, 25.2, 25.1, 24.0, 22.7, 21.6, 14.1, 8.6.

Anal. Calcd. for $C_{101}H_{194}N_3O_{17}P \cdot H_2O$: C, 68.47; H, 11.15; N, 2.37; P, 1.75. Found: C, 68.79; H, 11.00; N, 2.24; P, 1.97.

Examples 2-6

The primary objective of Examples 2-6 was to determine if RC-553 could promote minimal pyrogenicity and mediate adjuvant activity when formulated with vaccine antigens.

Example 2

Adjuvant Activity Towards HBsAg (Hepatitis B Surface Antigen)

Groups of BALB/c mice (Jackson Laboratories Bar Harbor, Me.) 6-8 weeks old were injected s.c. with 2 μg HBsAg (Laboratorio Pablo Cassara) ±20 μg adjuvant (MPL® immunostimulant or RC-553) on day 0 and day 21. Vaccines were prepared by mixing the adjuvant-containing TEoA (triethanolamine) formulations with recombinant HBsAg. Titers to HBsAg were determined by ELISA from pooled sera (5 mice/group) collected 21 days post-secondary vaccination (Table 1). The nonimmune controls were not vaccinated.

Serum titers from mice receiving RC-553 had anti-HBsAg responses significantly higher than control sera receiving antigen alone (Table 1). Especially noticeable was the increase in the titers for the IgG2a and IgG2b isotypes. These titers were equivalent to those expressed by control groups receiving MPL® immunostimulant.

TABLE 1

Comparison of Low Pyrogen Adjuvants with HBsAg

| Groups | Pyro-genicity[a] | Serum Titers | | | |
|---|---|---|---|---|---|
| | | IgG | IgG1 | IgG2a | IgG2b |
| Nonimmune | — | <100 | <100 | <100 | <100 |
| TEoA Vehicle | N.T. | 51,200 | 102,400 | 25,600 | 1600 |
| MPL®-TEoA | 2-3 | 409,600 | 204,800 | 204,800 | 51,200 |
| RC-553-TEoA | 0.3 | 409,600 | 204,800 | 409,600 | 51,200 |

[a]The pyrogenicity data represents the total rise in ° C. of 3 rabbits following i.v. administration of a 10 µg/Kg dose. In the pyrogen assay the compounds were solubilized in 10% EtOH/WFI(USP Water for Injection) at 100 µg/ml and then diluted with 5% dextrose in water.
N.T. means the compound was not tested.

Example 3

Adjuvant Activity Towards Hemagglutinin Protein in Fluzone Influenza Vaccine Groups of BALB/c mice (Jackson Laboratories Bar Harbor, Me.) 6-8 weeks old were injected subcutaneous with 0.2 µg hemagglutinin protein in FluZone influenza vaccine (Connaught Laboratories, Swiftwater, Pa.) ±20 µg adjuvant (MPL® immunostimulant or RC-553) on day 0 and day 14. Titers to FluZone were determined by FluZone ELISA from pooled sera of 5 mice collected 14 days post secondary (Table 2). The nonimmune controls were not vaccinated. The initial dilutions used on sera from test groups was 1:1600.

The results were similar to those in the previous Example. Again RC-553 had titers significantly higher than control sera receiving antigen alone (Table 2). The increase in titers was also reflected in the enhanced IgG2a and IgG2b responses. These titers were equivalent to those expressed by control groups receiving MPL® immunostimulant.

TABLE 2

Comparison of Low Pyrogen Adjuvants with an Influenza Vaccine

| Groups | Pyrogenicity[a] | Serum Titer | | | |
|---|---|---|---|---|---|
| | | IgG | IgG1 | IgG2a | IgG2b |
| Nonimmune | — | <100 | <100 | <100 | <100 |
| TEoA Vehicle | N.T. | 12,800 | 51,200 | 1600 | <1600 |
| MPL®-TEoA | 2-3 | 102,400 | 102,400 | 25,600 | 12,800 |
| RG-553-TEoA | 0.3 | 51,200 | 102,400 | 25,600 | 6400 |

[a]The pyrogenicity data represents the total rise in ° C. of 3 rabbits following i.v. administration of a 10 µg/Kg dose. In the pyrogen assay the compounds were solubilized in 10% EtOH/WFI(USP Water for Injection) at 100 µg/ml and then diluted with 5% dextrose in water.
N.T. means the compound was not tested.

Example 4

Adjuvant Activity Towards HBsAg

Groups of BALB/c mice injected subcutaneous with 2.0 µg HBsAg (Rhein Americana, & Rhein Biotech) ±25 µg adjuvant (MPL® immunostimulant or RC-553) on day 0 and day 21. IgG1 and IgG2a isotype titers to HBsAg were determined by ELISA from pooled sera collected 21 days post secondary (Table 3). The nonimmune controls were not vaccinated. In this experiment, RC-553 mediated increased titers compared to the control group, which received antigen in PBS. RC-553 stimulated titers equivalent to the positive controls, MPL® immunostimulant (Table 3).

TABLE 3

Comparison of Low Pyrogen Adjuvants with HBsAg

| Groups | Pyrogenicity[a] | Serum Titers | |
|---|---|---|---|
| | | IgG1 | IgG2a |
| Nonimmune | — | <100 | <100 |
| PBS Control | N.T. | 64,000 | 4000 |
| MPL®-TEoA | 2-3 | 128,000 | 1,024,000 |
| RC-553-TEoA | 0.3 | 32,000 | 2,048,000 |

[a]The pyrogenicity data represents the total rise in ° C. of 3 rabbits following i.v. administration of a 10 µg/Kg dose. In the pyrogen assay the compounds were solubilized in 10% EtOH/WFI(USP Water for Injection) at 100 µg/ml and then diluted with 5% dextrose in water.
N.T. means the compound was not tested.

Example 5

CTL Activity is Increased with RC-553 Towards HBsAg Immunized Mice

Some mice from each group of Example 4 were also used as spleen cell donors in order to evaluate CTL activity. HBsAg directed specific lysis was assessed in a standard four hour $^{51}$Cr-release assay (Moore et al., (1988) *Cell* 55: 777-785). Single cell suspensions were prepared from the spleens of mice 9 days post-vaccination. The spleen cells were treated with tris-buffered $NH_4Cl$ to remove erythrocytes and resuspended at a concentration of $7.5 \times 10^6$/ml in RPMI/10% FCS supplemented with 5 mM HEPES, 4 mM L-glutamine, 0.05 mM 2-mercaptoethanol and antibiotics. A synthetic peptide representing a known MHC class I, $L^d$-restricted CTL epitope (IPQSLDSWWTSL) was added to the cells at a final concentration of 75 nM. After a four day incubation, the cells were recovered and assessed for CTL activity. Specific killing was measured against $^{51}$Cr-labeled transfected P815S cells expressing the $L^d$-restricted epitope. The target cells were a transfected P815 cell line (P815S) which express the $L^d$-restricted CTL epitope. Non-specific lysis was <10% at an E:T of 50:1 against P815 target (Table 4) In contrast to the antibody response, RC-553 stimulated significantly elevated levels of CTL activity compared to the antigen only controls (Table 4).

TABLE 4

Comparison of Low Pyrogen Adjuvants with HBsAg

| Groups | Pyrogenicity[a] | Percent Specific Killing (Effector:Target Ratio) | | | |
|---|---|---|---|---|---|
| | | 50:1 | 25.1 | 12.5:1 | 6.25:1 |
| Nonimmune | — | 6 | 3 | 1 | 0 |
| PBS | N.T. | 29 | 20 | 11 | 7 |
| MPL®-TEoA | 2-3 | 80 | 71 | 47 | 32 |
| RC-553-TEoA | 0.3 | 85 | 77 | 53 | 37 |

[a]The pyrogenicity data represents the total rise in ° C. of 3 rabbits following i.v. administration of a 10 µg/Kg dose. In the pyrogen assay the compounds were solubilized in 10% EtOH/WFI(USP Water for Injection) at 100 µg/ml and then diluted with 5% dextrose in water.
N.T. means the compound was not tested.

Example 6

Ex Vivo Cytokine Induction by RC-553

The effects of RC-553 on the elaboration of TNF-α and IL-1β was measured under ex vivo conditions on human peripheral blood mononuclear cells. MPL® immunostimulant and RC-553 were formulated in aqueous solutions of 0.2% TEoA/WFI.

Human whole blood was used to evaluate the ability of glycolipids (AGPs) to induce proinflammatory cytokines. Human whole blood is collected into heparinized tubes and 0.45 ml of whole blood is admixed with 0.05 ml phosphate buffered saline (PBS, pH 7.4) containing the glycolipid (i.e., the test compounds). The tubes are incubated for 4 hr at 37° C. on a shaker apparatus. The samples are then diluted with 1.5 ml sterile PBS and centrifuged. The supernatants are removed and analyzed for cell associated TNF-α and IL-1β by sandwich ELISA using R&D Systems' Quantikine immunoassay kits for human TNF-α and IL-1β.

At 1, 5 and 10 μg/ml in the assay, RC-553 did not produce levels of TNF-α that could be detected under the condition of the assay. In contrast, the positive control LPS immunostimulant was effective at inducing TNF-α in the concentration range of 100 to 10,000 ng/mL.

Similarly, RC-553 (at 1, 5, and 10 μg/ml) did not produce detectable levels of IL-1β. To compare the effects of RC-553, the level of IL-1β induced with MPL® immunostimulant was assigned a value of 1 and relative induction of cytokines for RC-553 was $\leq 0.05$.

Discussion of Examples 2-6

The data from these studies indicate that RC-553 is able to enhance immunity to vaccine antigens. RC-553 enhanced serum titers to two distinct vaccine antigens, influenza and hepatitis surface antigens. Like MPL® immunostimulant, the RC-553 mediated a shift in the antibody profile from a response dominated by the IgG1 isotype to a response with high levels of IgG2a antibodies. In addition to enhancing the antibody response, RC-553 is a good adjuvant for inducing CTL activity.

A remarkable feature of the results in this study is that RC-553 appears to be influencing the response without inducing detectable levels of the inflammatory cytokines TNF-α or IL-1β. These cytokines are both produced by cells of the innate immune system in response to bacterial cell wall products including lipid A. Since RC-553 shares structural similarities with lipid A it is conceivable that it would also stimulate TNF-α or IL-1β and indeed many of AGP molecules do. As inflammatory cytokines TNF-α and IL-1β stimulate the release of cascades of other cytokine mediators responsible for activating phagocytic cells and mobilizing specific immunity. IL-1 was initially called endogenous pyrogen because it induces a fever response. Thus, the lack of detectable IL-1 following administration of RC-553 coincides with the apparent lack of fever in the rabbit pyrogen test.

It remains possible that RC-553 in these studies actually promotes the secretion of TNF-α and IL-1β at levels high enough to mediate activation of specific immunity yet too low to be detected in the ex vivo cytokine assay. Another option would be that these compounds stimulate cytokine mediators other than TNF-α and IL-1β that lead to a specific immune response to co-administered vaccine antigens. It seems likely that IFNγ is being produced. This cytokine is thought to be responsible for inducing the isotype switch to antibodies of the IgG2a subclass as well as being a promoter of TH-1 driven CTL responses. Thus the increased IgG2a titers and the active CTL populations both reflect the production of IFNγ.

Example 7

Inducible Nitric Oxide Synthase (Inos) Stimulation By RC-553

This example illustrates the effects of various glycolipids on iNOS induction in J774 murine macrophages. The murine macrophage cell line J774 can be primed by IFN-γ in vitro and is very responsive to subsequent LPS stimulation of iNOS upregulation as measured by a standard Greiss reagent ELISA assay procedure. The assay utilizes J774 cells seeded at $1 \times 10^6$/mL with 30 mL/flask and with IFN-γ added at 100 units/mL for 16-24 hrs. Cells are then harvested and washed and resuspended at $2 \times 10^5$/well in a 96-well plate and allowed to adhere. Glycolipid compounds are serially diluted into the wells for a test group and the resulting cultures are incubated for another 36-40 hrs before culture supernatants are collected from Greiss reagent analysis of nitrite release (Green et al. (1982) *Anal. Biochem.* 126: 131-138). Nitrite content closely parallels iNOS function.

Potency was determined as the concentration (ng/mL) of glycolipid in culture capable of inducing one-half maximal induction of nitrite ($ED_{50}$). The lower the $ED_{50}$ number, the greater the potency for iNOS induction. The ED50 was caclulated according to methods set out in Johnson et al., (1999) *J Med Chem.* 42: 4640-4649.

MPL® immunostimulant was found to have an $ED_{50}$ of about 2 ng/mL resulting in high levels of nitrite elaboration while RC-553 exhibited a nominal $ED_{50}$ of about $\geq 3000$ (ng/ml).

The very low maximal iNOS activity observed with RC-553 suggests that it is essentially inactive in this system for iNOS induction.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of inducing an immune response in a subject, the method comprising:

administering a composition comprising a therapeutically effective amount of a pharmaceutically acceptable carrier and a compound having the formula of:

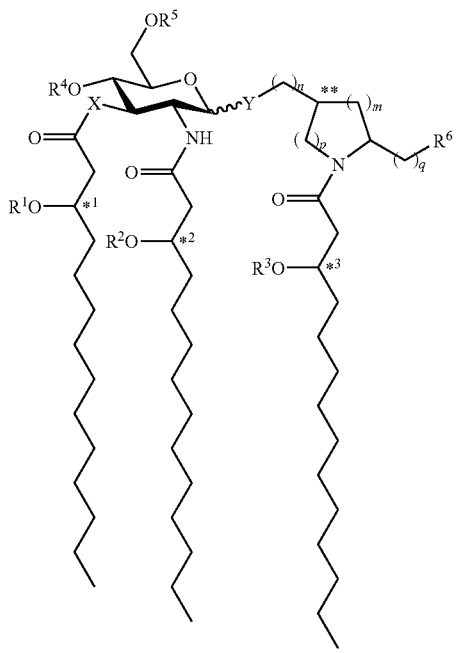

and pharmaceutically acceptable salts thereof, wherein X is a member selected from the group consisting of —O— and —NH—;

Y is a member selected from the group consisting of —O— and —S—;

$R^1$, $R^2$ and $R^3$ are each members independently selected from the group consisting of ($C_2$-$C_{24}$)acyl;

$R^4$ is a member selected from the group consisting of —H and —$PO_3R^7R^8$, wherein $R^7$ and $R^8$ are each members independently selected from the group consisting of —H and ($C_1$-$C_4$)alkyl;

$R^5$ is a member selected from the group consisting of —H, —$CH_3$ and —$PO_3R^9R^{10}$, wherein $R^9$ and $R^{10}$ are each members independently selected from the group consisting of —H and ($C_1$-$C_4$)alkyl;

$R^6$ is selected from H, OH, ($C_1$-$C_4$)alkoxy, —$PO_3R^{11}R^{12}$, —$OPO_3R^{11}R^{12}$, —$SO_3R^{11}$, —$OSO_3R^{11}$, —$NR^{11}R^{12}$, —$SR^{11}$, —CN, —$NO_2$, —CHO, —$CO_2R^{11}$, and —$CONR^{11}R^{12}$, wherein $R^{11}$ and $R^{12}$ are each independently selected from H and ($C_1$-$C_4$)alkyl, with the proviso that when $R^4$ is —$PO_3R^7R^8$, $R^5$ is other than —$PO_3R^9R^{10}$;

wherein "*1", "*2", "*3" and "**" represent chiral centers; wherein the subscripts n, m, p and q are each independently an integer from 0 to 6, with the proviso that the sum of p and m is from 0 to 6.

2. The method of claim 1, wherein X and Y are —O—, $R^4$ is $PO_3R^7R^8$, $R^5$ and $R^6$ are H, and the subscripts n, m, p, and q are integers from 0 to 3.

3. The method of claim 2, wherein $R^7$ and $R^8$ are —H.

4. The method of claim 3, subscripts n, m, p, and q are from 0 to 2.

5. The method of claim 3, wherein subscript n is 1, subscript m is 2, and subscripts p and q are 0.

6. The method of claim 5, wherein $R_1$, $R_2$, and $R_3$ are tetradecanoyl residues.

7. The method of claim 5, wherein *1, *2, and *3 are in the R configuration.

8. The method of claim 5, wherein Y is in the equatorial position.

9. The method of claim 5, wherein ** is in the S configuration.

10. The method of claim 5, wherein *1, *2, and *3 are in the R configuration, wherein Y is in the equatorial position, and wherein ** is in the S configuration.

11. The method of claim 5, wherein said composition further comprises at least one antigen.

12. A method of treating a mammal suffering from or susceptible to a pathogenic infection, cancer or an autoimmune disorder comprising administering to the mammal a therapeutically effective amount of a composition comprising a pharmaceutically acceptable carrier and a compound having the formula of:

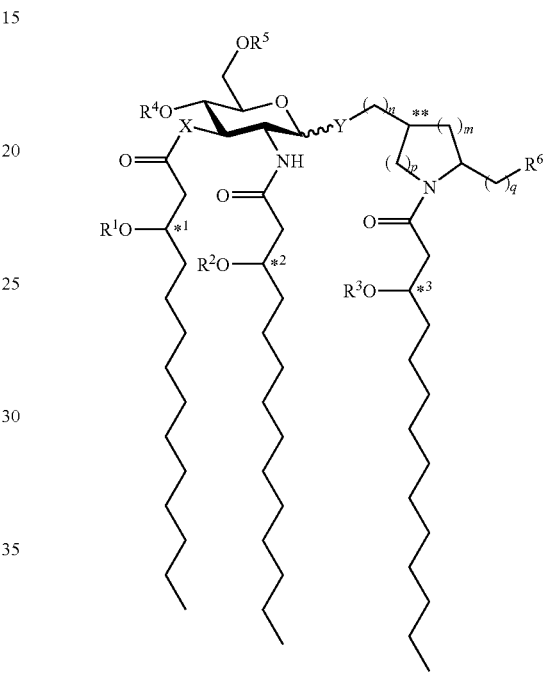

and pharmaceutically acceptable salts thereof, wherein X is a member selected from the group consisting of —O— and —NH—;

Y is a member selected from the group consisting of —O— and —S—;

$R^1$, $R^2$ and $R^3$ are each members independently selected from the group consisting of ($C_2$-$C_{24}$)acyl;

$R^4$ is a member selected from the group consisting of —H and —$PO_3R^7R^8$, wherein $R^7$ and $R^8$ are each members independently selected from the group consisting of —H and ($C_1$-$C_4$)alkyl;

$R^5$ is a member selected from the group consisting of —H, —$CH_3$ and —$PO_3R^9R^{10}$, wherein $R^9$ and $R^{10}$ are each members independently selected from the group consisting of —H and ($C_1$-$C_4$)alkyl;

$R^6$ is selected from H, OH, ($C_1$-$C_4$)alkoxy, —$PO_3R^{11}R^{12}$, —$OPO_3R^{11}R^{12}$, —$SO_3R^{11}$, —$OSO_3R^{11}$, —$NR^{11}R^{12}$, —$SR^{11}$, —CN, —$NO_2$, —CHO, —$CO_2R^{11}$, and —$CONR^{11}R^{12}$, wherein $R^{11}$ and $R^{12}$ are each independently selected from H and ($C_1$-$C_4$)alkyl, with the proviso that when $R^4$ is —$PO_3R^7R^8$, $R^5$ is other than —$PO_3R^9R^{10}$;

wherein "*1", "*2", "*3" and "**" represent chiral centers; wherein the subscripts n, m, p and q are each independently an integer from 0 to 6, with the proviso that the sum of p and m is from 0 to 6.

13. The method of claim 12, wherein X and Y are —O—, $R^4$ is $PO_3R^7R^8$, $R^5$ and $R^6$ are H, and the subscripts n, m, p, and q are integers from 0 to 3.

14. The method of claim 13, wherein $R^7$ and $R^8$ are —H.

15. The method of claim 14, subscripts n, m, p, and q are from 0 to 2.

16. The method of claim 14, wherein subscript n is 1, subscript m is 2, and subscripts p and q are 0.

17. The method of claim 16, wherein $R_1$, $R_2$, and $R_3$ are tetradecanoyl residues.

18. The method of claim 16, wherein *¹, *², and *³ are in the R configuration.

19. The method of claim 16, wherein Y is in the equatorial position.

20. The method of claim 16, wherein ** is in the S configuration.

21. The method of claim 16, wherein *¹, *², and *³ are in the R configuration, wherein Y is in the equatorial position, and wherein ** is in the S configuration.

22. The method of claim 12, wherein said composition further comprises at least one antigen.

23. A method for treating diseases or conditions ameliorated by nitric oxide production in a subject comprising contacting said subject with an effective amount of a compound of the formula:

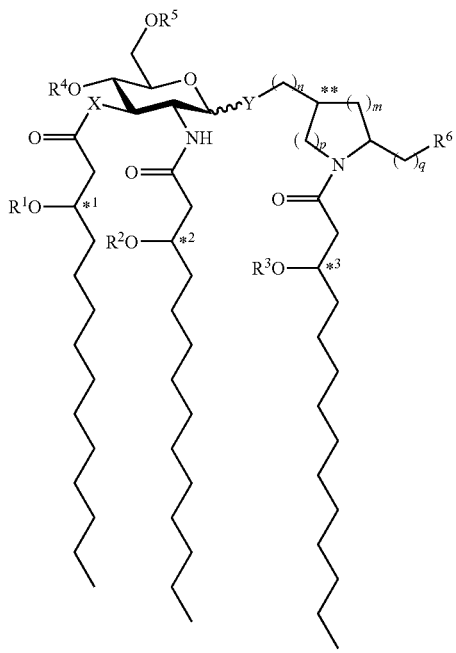

and pharmaceutically acceptable salts thereof, wherein X is a member selected from the group consisting of —O— and —NH—;

Y is a member selected from the group consisting of —O— and —S—;

$R^1$, $R^2$ and $R^3$ are each members independently selected from the group consisting of $(C_2-C_{24})$acyl;

$R^4$ is a member selected from the group consisting of —H and —$PO_3R^7R^8$, wherein $R^7$ and $R^8$ are each members independently selected from the group consisting of —H and $(C_1-C_4)$alkyl;

$R^5$ is a member selected from the group consisting of —H, —$CH_3$ and —$PO_3R^9R^{10}$, wherein $R^9$ and $R^{10}$ are each members independently selected from the group consisting of —H and $(C_1-C_4)$alkyl;

$R^6$ is selected from H, OH, $(C_1-C_4)$alkoxy, —$PO_3R^{11}R^{12}$, —$OPO_3R^{11}R^{12}$, —$SO_3R^{11}$, —$OSO_3R^{11}$, —$NR^{11}R^{12}$, —$SR^{11}$, —CN, —$NO_2$, —CHO, —$CO_2R^{11}$, and —$CONR^{11}R^{12}$, wherein $R^{11}$ and $R^{12}$ are each independently selected from H and $(C_1-C_4)$alkyl, with the proviso that when $R^4$ is —$PO_3R^7R^8$, $R^5$ is other than —$PO_3R^9R^{10}$;

wherein "*¹", "*²", "*³" and "**" represent chiral centers;

wherein the subscripts n, m, p and q are each independently an integer from 0 to 6, with the proviso that the sum of p and m is from 0 to 6.

24. A method in accordance with claim 23, wherein said compound is administered to said animal during the period from about 48 hours prior to the onset of ischemia, up to onset of ischemia.

25. A method in accordance with claim 23, wherein said compound is administered to said animal from immediately prior to the onset of ischemia through ischemia.

26. A method in accordance with claim 23, wherein said compound is administered to said animal from immediately prior to the onset of ischemia through reperfusion.

27. A method in accordance with claim 23, wherein X and Y are —O—, $R^4$ is $PO_3R^7R^8$, $R^5$ and $R^6$ are H, wherein $R^7$ and $R^8$ are —H, wherein subscript n is 1, subscript m is 2, and subscripts p and q are 0, wherein $R_1$, $R_2$, and $R_3$ are tetradecanoyl residues, wherein *¹, *², and *³ are in the R configuration, wherein Y is in the equatorial position, and wherein ** is in the S configuration.

* * * * *